(12) United States Patent
Theriault et al.

(10) Patent No.: US 11,480,526 B2
(45) Date of Patent: Oct. 25, 2022

(54) INSTRUMENT FOR SEQUENTIAL ANALYSIS FOR SILICA AND PHOSPHATE IN AQUEOUS SOLUTION

(71) Applicant: Mettler-Toledo Thornton, Inc., Billerica, MA (US)

(72) Inventors: Robert Theriault, Tyngsborough, MA (US); David Marsh, Tewksbury, MA (US); Anthony C. Bevilacqua, Jr., Medford, MA (US)

(73) Assignee: Mettler-Toledo Thornton, Inc., Billerica, MA (US)

( * ) Notice: Subject to any disclaimer, the term of this patent is extended or adjusted under 35 U.S.C. 154(b) by 164 days.

(21) Appl. No.: 16/748,097

(22) Filed: Jan. 21, 2020

(65) Prior Publication Data
US 2021/0223184 A1    Jul. 22, 2021

(51) Int. Cl.
*G01N 21/78* (2006.01)
*B01L 3/00* (2006.01)

(52) U.S. Cl.
CPC .............. *G01N 21/78* (2013.01); *B01L 3/502* (2013.01); *B01L 2200/0605* (2013.01);
(Continued)

(58) Field of Classification Search
CPC ................. G01N 21/78; G01N 33/182; G01N 2021/7793; G01N 33/1893;
(Continued)

(56) References Cited

U.S. PATENT DOCUMENTS

| | | |
|---|---|---|
| 5,550,053 A | 8/1996 | Salpeter |
| 7,416,899 B2 | 8/2008 | Kaneko et al. |
| | (Continued) | |

FOREIGN PATENT DOCUMENTS

| | | |
|---|---|---|
| CN | 2695974 Y | 4/2005 |
| CN | 102226755 A | 10/2011 |
| | (Continued) | |

OTHER PUBLICATIONS

Giusto et al. ACS Publications Omega 2018 7517-7522. (Year: 2018).*

(Continued)

*Primary Examiner* — Benjamin R Whatley
*Assistant Examiner* — John McGuirk
(74) *Attorney, Agent, or Firm* — Standley Law Group LLP; Jeffrey S. Standley; Stephen L. Grant (57) ABSTRACT

A sample of water is tested for silica and phosphate content in a single apparatus. In the test method, a first sample of the water is colorimetrically analyzed in a reaction chamber using a "molybdenum blue" test in which silica and phosphate in the sample are complexed with a first reagent. The phosphate complexes are then optically inactivated by a second reagent and the color of the silica complexes is intensified with a third reagent. From this, the silica content is calculated. A further sample is colorimetrically analyzed without using the second reagent, so that a combined silica and phosphate content of the further sample is obtained. A value of the silica content is subtracted from the value of the combined silica and phosphate content, resulting in a phosphate content for the sample. The silica content and the phosphate content of the sample are reportable.

10 Claims, 4 Drawing Sheets

(52) U.S. Cl.
CPC ..... *B01L 2200/148* (2013.01); *B01L 2200/16* (2013.01); *B01L 2300/0663* (2013.01); *B01L 2300/168* (2013.01); *B01L 2300/1805* (2013.01); *B01L 2400/06* (2013.01)

(58) Field of Classification Search
CPC  G01N 2021/7763; G01N 21/31; B01L 3/502; B01L 2200/0605; B01L 2200/148; B01L 2200/16; B01L 2300/0663; B01L 2300/168; B01L 2300/1805; B01L 2400/06
See application file for complete search history.

(56) References Cited

U.S. PATENT DOCUMENTS

| | | | |
|---|---|---|---|
| 10,119,951 | B2 | 11/2018 | Butcher et al. |
| 2012/0045369 | A1* | 2/2012 | Greensted ............... G01N 21/78 422/82.05 |
| 2012/0258542 | A1 | 10/2012 | Kathe et al. |
| 2013/0330245 | A1* | 12/2013 | Duncan ............. B01L 3/502715 422/502 |
| 2014/0273052 | A1* | 9/2014 | Reddy .................... G01N 21/77 435/25 |
| 2015/0377848 | A1* | 12/2015 | Shubat .................. G01N 21/31 422/82.09 |

FOREIGN PATENT DOCUMENTS

| | | | |
|---|---|---|---|
| CN | 101509904 B | | 11/2011 |
| CN | 102375068 A | | 3/2012 |
| CN | 106841182 A | * | 6/2017 |
| GB | 1417560 | | 12/1975 |
| JP | H11-237373 A | | 8/1999 |
| JP | 4465434 B2 | | 3/2010 |

OTHER PUBLICATIONS

El-Sayed, A.-A. Y. et al., Simultaneous Determination of Phosphate and Silicate by First-Derivative Spectrophotometry, Analytical Sciences, Dec. 2001, pp. 1461-1464, vol. 17.

Galhardo, C. X. et al., Spectrophotometric determination of phosphate and silicate by sequential injection using molybdenum blue chemistry, Analytica Chimica Acta, 2000 pp. 191-200, 417.

Grudpan, K. et al., Stopped-flow injection simultaneous determination of phosphate and silicate using molybdenum blue, Talanta, 2002, 1319-1326, 58.

Li, Y.-S. et al., Simultaneous determination of silicate and phosphate in boiler water at power plants based on series flow cells by using flow injection spectrophotometry, Analytica Chimica Acta, 2002, pp. 315-325, 455.

Mettler-Toledo Thornton, Inc., Power Industry, Process Analytical Solutions, Optimizing Power Plan Chemistry, Aug. 2016, 16 pages.

ASTM International, Standard Test Method for On-Line Colorimetric Measurement of Silica, Aug. 2015, 3 pages, D7126-15.

Mas-Torres, F. et al., Simultaneous Determination of Phosphate and Silicate in Waste Water by Sequential Injection Analysis, Analyst, Oct. 1997, pp. 1033-1038, vol. 122.

* cited by examiner

INSTRUMENT FOR SEQUENTIAL ANALYSIS FOR SILICA AND PHOSPHATE IN AQUEOUS SOLUTION

CROSS-REFERENCE TO RELATED APPLICATIONS

This application is a non-provisional application and makes no claim of priority.

TECHNICAL FIELD

The present invention relates to a single instrument, and a method for operating the single instrument, for analyzing the amounts of silica and phosphate present in a water sample.

BACKGROUND ART

In at least a few industries, there is a need to provide "ultrapure" water, that is, water that is required to meet uncommonly strict purity standards. In manufacturing applications, "ultrapure" water may be required in the electronics, optical and pharmaceutical industries. The term "ultrapure" is also found in the power industry, where the standards for purity of makeup water for raising steam, especially with regard to silica content, are uncommonly high. In this latter case, the makeup water may be required that has a silica content that is below a very low standard but which also must have a phosphate content that exceeds a predetermined minimum standard, to maintain pH levels as a protection against corrosion.

In the known prior art, devices are known for determining silica content, using a known and accepted international standard test. However, such devices are not known for monitoring phosphate content in the same device, so that a single device can provide an analysis for both silica and phosphate.

It is therefore, an unmet object of the prior art to provide a single device and method that analyzes for both silica and phosphate.

SUMMARY

This and other unmet object of the prior art are met by a method and a device having a controller programmed to perform the method. In a method for analyzing a sample of water for silica and phosphate content in a single apparatus, the method comprises the steps of:

providing, in a reaction chamber of the apparatus, a water sample to be analyzed;

obtaining, in the apparatus, a value of a silica content of the water sample;

storing the value of the obtained silica content in a database in communication with the apparatus;

rinsing and refilling the reaction chamber with a further water sample;

obtaining, in the apparatus, a value of a combined silica and phosphate content of the further water sample; and calculating a phosphate content of the further water sample by comparing the value of the combined silica and phosphate content to a representative value of the silica content stored in the database.

In some of the embodiments, the step of providing the water sample to be analyzed is achieved by sub-steps comprising:

rinsing the reaction chamber with the water to be sampled by flowing the water to be sampled therethrough;

stopping the flow through the reaction chamber of the water to be sampled, retaining a water sample in the reaction chamber; and passing light from a light source across the reaction chamber through the water sample to a photodetector, measuring the current generated thereby in the photodetector and storing the current as a baseline value in the database.

In many of the embodiments, the step of obtaining the value of the silica content of the water sample is achieved by sub-steps comprising:

adding a first reagent to the water sample, the first reagent selected to react with silica and phosphate in the water sample, producing colored silica complexes and phosphate complexes, passing light from a light source across the reaction chamber through the water sample containing the colored silica and phosphate complexes to a photodetector, measuring the current generated thereby in the photodetector and storing the current as a first silica value in the database;

adding a second reagent to the water sample containing the colored silica complexes and phosphate complexes, the second reagent selected to react with only with the colored phosphate complexes, which are converted into an optically-inactive phosphate moiety;

passing light from the light source across the reaction chamber through the water sample containing the colored silica complexes and the optically-inactive phosphate moiety to the photodetector, measuring the current generated thereby in the photodetector and storing the current as a second silica value in the database;

adding a third reagent to the water sample containing the colored silica complexes and the optically-inactive phosphate moiety, the third reagent selected to react with only the colored silica complexes, which are converted into more intensely colored silica complexes;

passing light from the light source across the reaction chamber through the water sample, containing the more intensely colored silica complexes and the optically-inactive phosphate moiety, to the photodetector, measuring the current generated thereby in the photodetector and storing the current as a third silica value in the database; and calculating, in a processor in communication with the database, the value of the silica content in the water sample from a relationship between the third silica value and at least one of the baseline value, the first silica value and the second silica value.

In many of the embodiments, the step of obtaining the value of the combined silica and phosphate content in the further water sample is achieved by sub-steps comprising:

adding the first reagent to the further water sample, producing colored silica complexes and phosphate complexes, passing light from a light source across the reaction chamber through the water sample containing the colored silica and phosphate complexes to a photodetector, measuring the current generated thereby in the photodetector and storing the current as a first combined value in the database;

adding the third reagent to the further water sample containing the colored silica and phosphate complexes, the third reagent selected to react with the colored silica complexes and the colored phosphate complexes, both of which are converted into more intensely colored complexes;

passing light from the light source across the reaction chamber through the further water sample, containing the more intensely colored complexes, to the photodetector, measuring the current generated thereby in the photodetector and storing the current as a second combined value in the database; and calculating, in a processor in communication with the database, the value of the combined silica and phosphate in the further water sample from a relationship between the second combined value and the first combined value.

In many of the embodiments, the step of calculating the phosphate content of the further water sample is achieved by substeps comprising:

determining the representative value of the silica content by using at least one silica content obtained before or after the combined silica and phosphate content; and obtaining the phosphate content by subtracting the representative value of the silica content from the combined silica and phosphate content.

In the preferred embodiments, the first reagent is an aqueous solution of ammonium molybdate and an inorganic acid; the second reagent is an aqueous solution of oxalic acid; and the third reagent is an aqueous solution of potassium disulfite and 4-(methylamino)phenol hemisulfate salt.

In the preferred embodiments, the light source produces monochromatic light having a wavelength of 815 nm.

In many embodiments, the step of rinsing and refilling the reaction chamber with a further water sample is achieved by sub-steps comprising:

rinsing the reaction chamber with the water to be sampled by flowing the water to be sampled therethrough;

stopping the flow through the reaction chamber of the water to be sampled, retaining a water sample in the reaction chamber; and passing light from a light source across the reaction chamber through the water sample to a photodetector, measuring the current generated thereby in the photodetector and storing the current as a baseline value in the database.

An apparatus for practicing the method of analyzing a water sample for both silica and phosphate content in a single apparatus comprises:

an inlet for receiving a stream of the water sample to be tested;

an exit for exhausting the water sample after testing;

a flow conduit, providing a liquid flow path from the inlet to the exit;

a reaction chamber, located in the flow conduit, sized to retain a predetermined volume of the water sample and comprising:

a sample inlet in liquid communication with the inlet;
a sample outlet in liquid communication with the exit;
a plurality of reagent inlets; and
a colorimetry apparatus comprising a window through which light is directed into the volume of the reaction chamber, a reflector for reflecting the light that is incident thereon back into the volume of the reaction chamber and a window through which the reflected light is received by a photodetector;

a valve for controlling flow through the flow conduit into the reaction chamber;

a plurality of reagent feed systems, each of which is in fluid communication with one of the plurality of reagent inlets; and a processor, in communication with the colorimetery apparatus, the valve and the plurality of reagent feed systems, programmed to operate the apparatus according to the method of claim 1.

Many embodiments of the apparatus will further comprise a heater, positioned in the flow conduit between the inlet and the valve, for selectively heating the water sample passing therethrough.

In many embodiments, each reagent feed system comprises a reagent container and a metering pump, selectively actuated by the processor to provide a predetermined amount of a selected reagent to one of the reagent inlets.

In many embodiments, the apparatus further comprises a calibration feed system comprising a calibration fluid container and a metering pump, selectively actuated by the processor to provide a predetermined amount of a selected calibration fluid to the flow conduit upstream of the valve.

BRIEF DESCRIPTION OF THE DRAWINGS

The inventive concepts will be better understood when reference is made to the drawings and the detailed description, wherein identical parts are identified using identical reference numbers and wherein.

DETAILED DESCRIPTION

Apparatus

Figure 1:
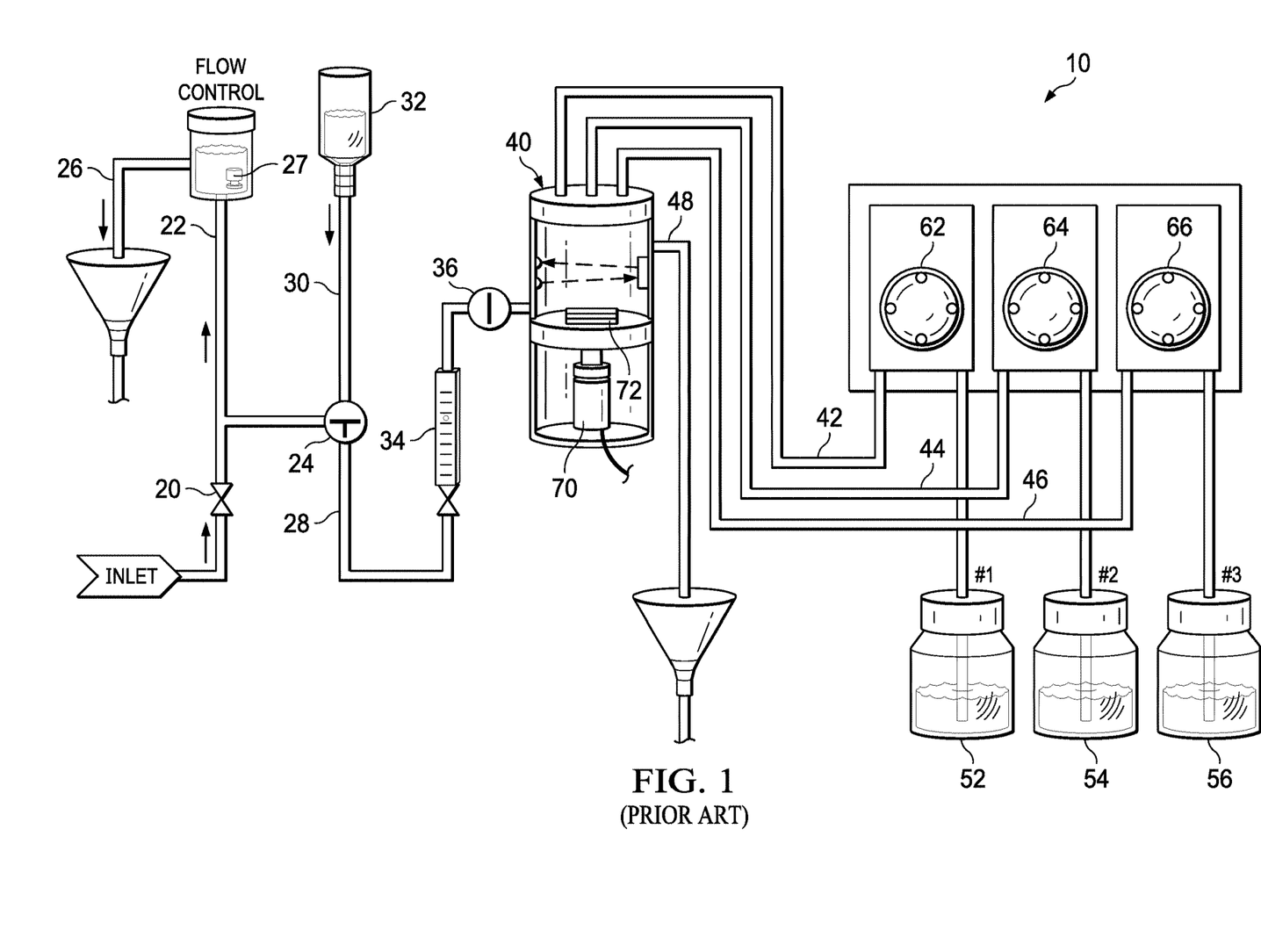
FIG. 1 is a schematic view of the flow path provided in a silica analyzing device as known in the prior art.

FIG. 1 shows a schematic view of the flow path provided by the prior art silica analyzing device 10. A valve 20, preferably a needle valve that allows precise flow control, establishes a flow rate within a sample line 22 that continuously receives a portion of the process fluid that can be analyzed. At least a portion of the process fluid passing needle valve 20 always flows to an outlet 26. A float switch 27 near the outlet 26, as well as sample line 22, maintains a pressure head to provide flow into the analyzing device 10. If entry of the process fluid from the sample line 22 into an analytical section of the device 10 is precluded by valve 24, all process fluid flows to the outlet 26. This flow assists in keeping the sample line 22 free of contaminants.

Valve 24 is preferably a multiple-port valve and is even more preferably an automated valve that controls fluid flow into the analytical section of the device 10. In a first position, process fluid in the sample line 22 is admitted into an analytical feed line 28 of the analytical section. In a second position, fluid from an alternate feed line 30 is admitted into the analytical feed line 28. The alternate feed line 30 has an insertion point 32, from which a manual sample, a calibration standard sample, or the like may be inserted. When the valve 24 is a three-way valve, as depicted here, it can close the analytical feed line 28 to all flow, although this capability is not usually used.

Flow through the analytical feed line 28 may be confirmed by a flow meter 34, especially a volumetric flowmeter, positioned between valve 24 and valve 36. The depicted embodiment shows the flow meter 34 as a gravity-type flow meter or rotameter, in which the upward flow of the liquid operates against the downward force of gravity to balance a floating element in a flow channel having a flow area that increases from the bottom to the top thereof. In an alternative embodiment, a flow meter providing a digital output flow signal may be used. In either case, this flowmeter 34 both verifies flow and provides a feedback in adjusting flow through valve 20. Valve 36 is preferably a two-way valve, and is more preferably an automated valve, providing "on/off" control of sample fluid flow into a reaction chamber 40.

The reaction chamber 40 has several inputs other than sample fluid flow that passes through valve 36. Three of these inputs 42, 44 and 46, are from reagent sources 52, 54 and 56, by way of metering pumps 62, 64, 66. Typically, these metering pumps 62, 64, 66 will be peristaltic pumps. Reaction chamber 40 also has an outlet 48, for exhausting fluids subsequent to an analysis. Preferably, reaction chamber 40 is provided with a means for stirring, depicted in FIG. 1 as a magnetic stirring motor 70 and a stir bar 72. In the preferred embodiments, the fluid being sampled enters low in the reaction chamber and exits through an overflow line 48.

Figure 2:
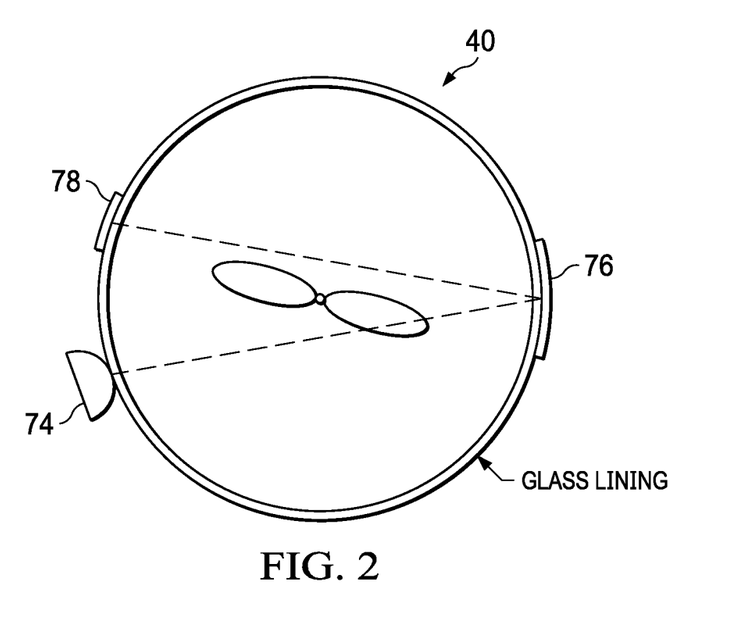
FIG. 2 is a schematic top plan view of the interior of the reaction chamber.

FIG. 2 shows a top plan view into the reaction chamber 40. As the test performed therein is a colorimetric test, the chamber 40 has a first window 74, into which light can be directed, a reflector 76 on an opposing wall of the chamber and a second window 78 for a photodetector, typically in the nature of a photodiode, to collect light that has passed through the chamber and been reflected off of the reflector. This colorimetric test will be described in more detail below. When viewed from the side, it would be noted that the first window 74, the reflector 76 and the second window 78 are located at the same elevation, which is preferably about halfway between the inlet line and the overflow line 48.

Figure 3:
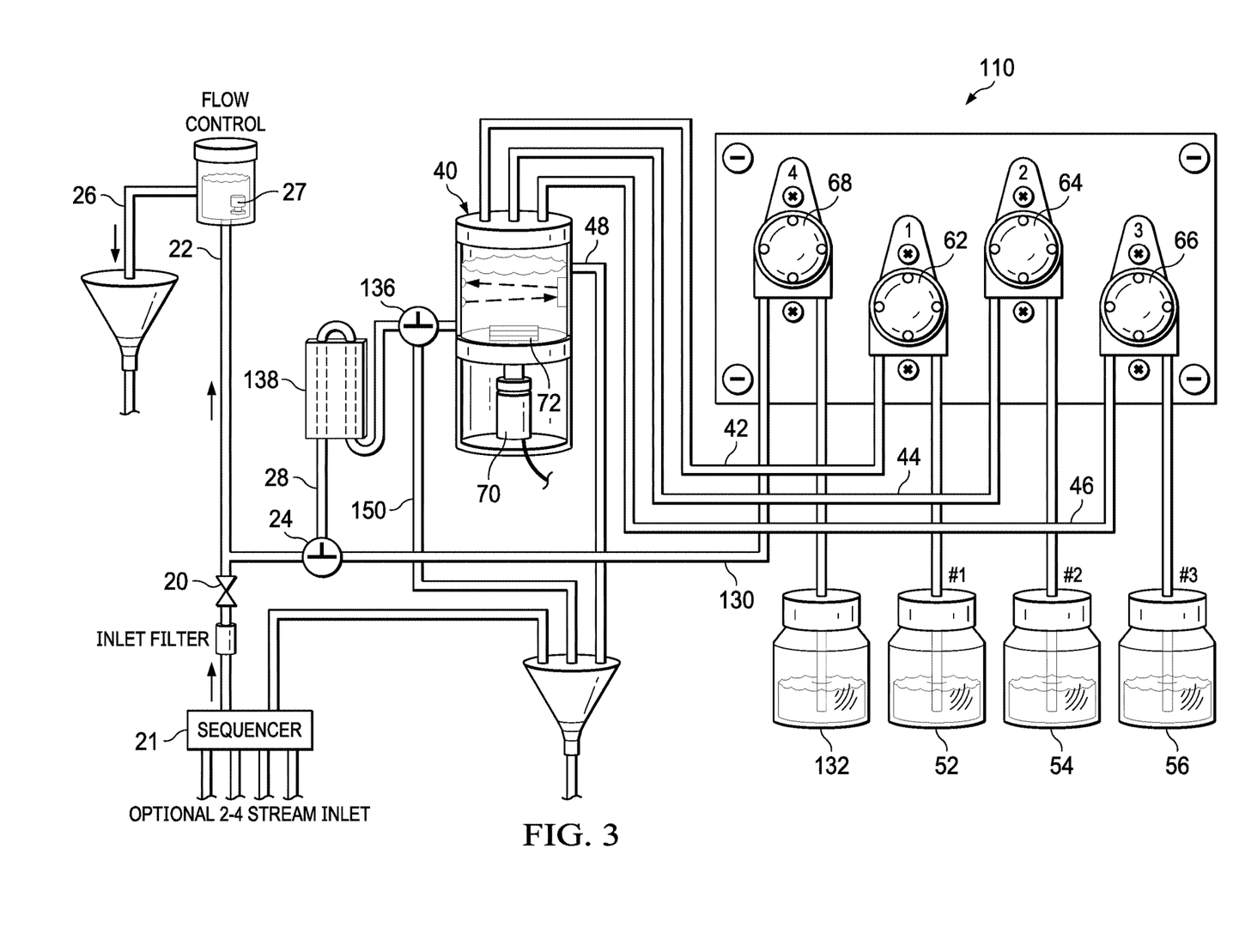
FIG. 3 is a schematic view of the flow path provided in a device for analyzing both silica and phosphate, according to the inventive concept.

FIG. 3 shows a schematic view of the flow path provided by a silica analyzing device 110 that has been modified to provide analysis for both silica and phosphate, that is, the inventive concept. A valve 20, preferably a needle valve that allows precise flow control, establishes a flow rate within a sample line 22 that continuously receives a portion of the process fluid that can be tested. In the depicted embodiment, the valve 20 receives input from a sequencer 21, which can allow an input to be selected from a plurality of streams. As in FIG. 1, at least a portion of the process fluid in sample line 22 always flows to outlet 26. If there is no flow at outlet 26, as determined by a float switch or the like, operation of the device is stopped. If entry of the process fluid from the sample line 22 into an analytical section of the device 110 is precluded by valve 24, the process fluid flows to an outlet 26. This flow assists in keeping the sample line 22 free of contaminants.

As in the prior art embodiment, valve 24 is preferably a three-way valve and is even more preferably an automated valve that controls fluid flow into the analytical section of the device 110. In a first position, process fluid in the sample line 22 is admitted into an analytical feed line 28 of the analytical section. In a second position, fluid from an alternate feed line 130 is admitted into the analytical feed line 28. The alternate feed line 130 in this embodiment is fed from an insertion point 132, from which a manual sample, a calibration standard sample, or the like may be inserted. Unlike the prior art embodiment, the fluid from insertion point 132 does not flow by gravity to valve 24, but is instead lifted by a pump 68, preferably a peristaltic pump. In the third position of valve 24, all flow through valve 24 to analytical feed line 28 can be shut off, although, as in FIG. 1, this is a capability that is not usually used.

Downstream of valve 24, analytical feed line 28 is shown to pass through a heater 138 to condition the fluid, if necessary, before arriving at valve 136. While not present in the prior art device, the heater 138 provides the valuable advantages of supporting a reduced cycle time in performing the analysis, as well as providing a more consistent temperature for conducting the analysis. Valve 136 is depicted as a two-way valve in this instance. In a first position, flow from analytical feed line 28 is directed to the reaction chamber 40, while in a second position, the valve may be used to drain reaction chamber 40 to drain line 150.

Since the same basic reactions will be occurring in reaction chamber 40 in the modified analyzer 110, it will be seen to have effectively the same configuration as in the prior art analyzer 10 of FIG. 1. In addition to the input through valve 136, reaction chamber 40 has inputs 42, 44 and 46 from reagent sources 52, 54 and 56, by way of metering pumps 62, 64, 66. The preferred metering pumps 62, 64, 66 are peristaltic pumps in which the reagents being pumped are contained within flexible tubing to prevent contamination. Reaction chamber 40 also has an outlet 48, for draining fluids subsequent to an analysis. Preferably, reaction chamber 40 is provided with a means for stirring, depicted in FIG. 1 as a magnetic stirring motor 70 and a stir bar 72.

A top plan view of reaction chamber 40 for device 110 is identical to the view shown in FIG. 2.

Chemistry

The basic chemistry of silica analysis that has been used in the prior art device is known and is standardized by ASTM International (ASTM-I), an organization that develops and publishes voluntary consensus technical standards, as ASTM D7126, with the title "Standard On-line Colorimetric Measurement of Silica." The method is informally referred to as the "molybdenum blue" or the "heteropoly blue" method. ASTM-I indicates that it is applicable for determining silica in water in the range of 0.5 to 5000 ppb. ASTM-I also indicates that the test method covers the determination of soluble silica $SiO_2$ (silicon dioxide) or silicates in water. Soluble silica compounds are considered molybdate reactive silica. This test method does not cover the determination of colloidal or polymeric silica, which is considered non-molybdate reactive silica.

Referring to the prior art device shown in FIG. 1, the reactor chamber 40 is rinsed by flowing the process fluid to be tested through the chamber. After a prescribed rinsing period, an aliquot of the process fluid is held in the reaction chamber as the test sample and the flow is stopped.

At the conclusion of the stabilization period, a monochromatic light is projected from a light-source through window 74 across the reaction chamber, where the light reflects off of reflector 76 and traverses the test sample a second time to be received at the photodetector in window 78. The light received at the photodetector is measured by the photodetector, in a measurement referred to as $E_b$, or the "blank current." The preferred light source is a light-emitting diode (LED) that is powered by a fixed current drive supply to assure consistent light output throughout these steps. The preferred wavelength is 815 nm for the molybdate complex chemistry being used here, so all references in describing the preferred method will refer to that wavelength. While it is possible to use other wavelengths (or multiple wavelengths), it is clearly preferred to use a light source providing 815 nm light.

Once $E_b$ is established, an aliquot of up to 1 ml of Reagent 1 is added to the reaction chamber 40, from reagent source 52 through pump 62. Reagent 1 comprises an aqueous solution of ammonium molybdate with an inorganic acid.

The means for stirring the contents of the reaction chamber may or may not be operational at this point.

Reagent 1 immediately reacts with silica and phosphate present in the test sample. Molybdate complexes, yellow in color, of silica and phosphate are formed. The reaction is allowed to proceed for a predetermined reaction period. The molybdate complexes formed will each absorb marginal amounts of 815 nm light during this step. The current at the photodetector is monitored, and the current measured at the end of the reaction period is referred to as E2.

At this point, up to 1 ml of Reagent 2 is added to the reaction chamber 40 from reagent source 54 through pump 64. As before, the means for stirring may or may not be operating. Reagent 2 is an aqueous solution of oxalic acid, which reacts with any phosphate-molybdate complex present in the reaction chamber, breaking down the phosphate-molybdate complex into an optically inactive moiety, specifically one that does not absorb light at 815 nm. Oxalic acid does not appreciably affect the silica-molybdate complex present. After allowing the reaction to proceed for a predetermined reaction time, the current at the photodetector is again measured. The value obtained, denominated E3, should be greater than E2, as the phosphate-molybdate complex will no longer absorb.

At this point, an aliquot of Reagent 3 is added to reaction chamber 40 from reagent source 56 through pump 66. Reagent 3 is an aqueous solution of potassium disulfite and 4-(methylamino)phenol hemisulfate salt. The stirring means may or may not be operational. The reaction of the silica-molybdate complex with Reagent 3 generates a new complex having an intense blue color so the amount of 815 nm light absorbed strongly increases, reducing the amount of light received at the photodetector 78. After a predetermined reaction time, the current is measured at the photodetector 78. This measurement is designated E4.

Beer's law is a well-known principle of chemistry. According to Beer's law:

$$A = -\log(Ef/Ei) = \varepsilon b c.$$

wherein A is the absorbance, Ei is the initial current, Ef is the final current, $\varepsilon$ is the molar extinction coefficient, b is the pathlength of the optical sample and c is the concentration of the optically active species.

Rearranging the equation and solving for c, which is the measurement of interest, it is seen that $$c = -\log(Ef/Ei)/\varepsilon b.$$

Of these quantities, both currents have been measured and the product $\varepsilon b$ is a constant that has been predetermined from a calibration of the device and stored in memory of a processor operating the device. While the equation is accurate at lower concentrations, some corrections for deviations from ideality of Beer's Law, may need to be applied at higher concentrations. This is the basic working chemistry for the prior art silica analyzers. To complete the cycle, it is necessary to rinse the reaction chamber 40 with process fluid and to re-establish Eb. From beginning to end, the existing technology requires about 20 minutes for a cycle.

The above steps describe the measurement of silica in water, but this does not measure for phosphate, as the phosphate was removed by the addition of Reagent 2.

However, it is possible under the inventive concept to also measure phosphate in the test fluid, on an optional basis. To practice the inventive concept, the silica content of the process fluid is determined, using the process set forth above. That process ends with a reaction chamber that has been rinsed, ready for a new determination of Eb Then, an aliquot of up to 1 ml of Reagent 1 is added to the reaction chamber 40, from reagent source 52 through pump 62. The means for stirring the contents of the reaction chamber may or may not operational at this point.

As in the silica determination, Reagent 1 immediately reacts with silica and phosphate present in the test sample. The yellow molybdate complexes are formed. The reaction is allowed to proceed, but if the heater 138 is providing temperature control, the predetermined reaction time can be reduced. The molybdate complexes formed will each absorb marginal amounts of 815 nm light during this step. The current at the photodetector is monitored, and the current measured at the end of the reaction period is referred to as E2.

At this point, the step of injecting Reagent 2 to break down the phosphate molybdate complexes and render the phosphate optically inactive is not performed. Elimination of this step does not significantly shorten the overall process time, because the predetermined reaction time for the step in the silica analysis is short, relative to the time for other steps.

The reaction chamber 40 now contains the process fluid with both silica molybdate complexes and phosphate molybdate complexes. Adding an aliquot of Reagent 3 to reaction chamber 40 from reagent source 56 through pump 66 generates the intense blue color so the amount of 815 nm light absorbed strongly increases, reducing the amount received at the photodetector. Because the blue color is now attributable to both silica and phosphate complexes of the molybdate, the amount of 815 nm light at the photodetector is even further reduced from the silica determination. This measurement is denominated E4.

Once this value of E4 is obtained, Beer's Law is again applied, using the value of Eb determined at the beginning of the phosphate-determination cycle. The concentration c that results is the concentration of silica plus phosphate. When the absorbances from this test and from at least one "silica only" test are compared, the phosphate content is determinable by difference.

It is useful to recall that in a typical power plant water system, the acceptable level of silica will be very low, while the objective is to maintain a consistent positive level of phosphate, to maintain pH and prevent corrosion. For that reason, the silica plus phosphate concentration in that application will, generally, be close to a "phosphate alone" determination.

Algorithm

Figure 4:
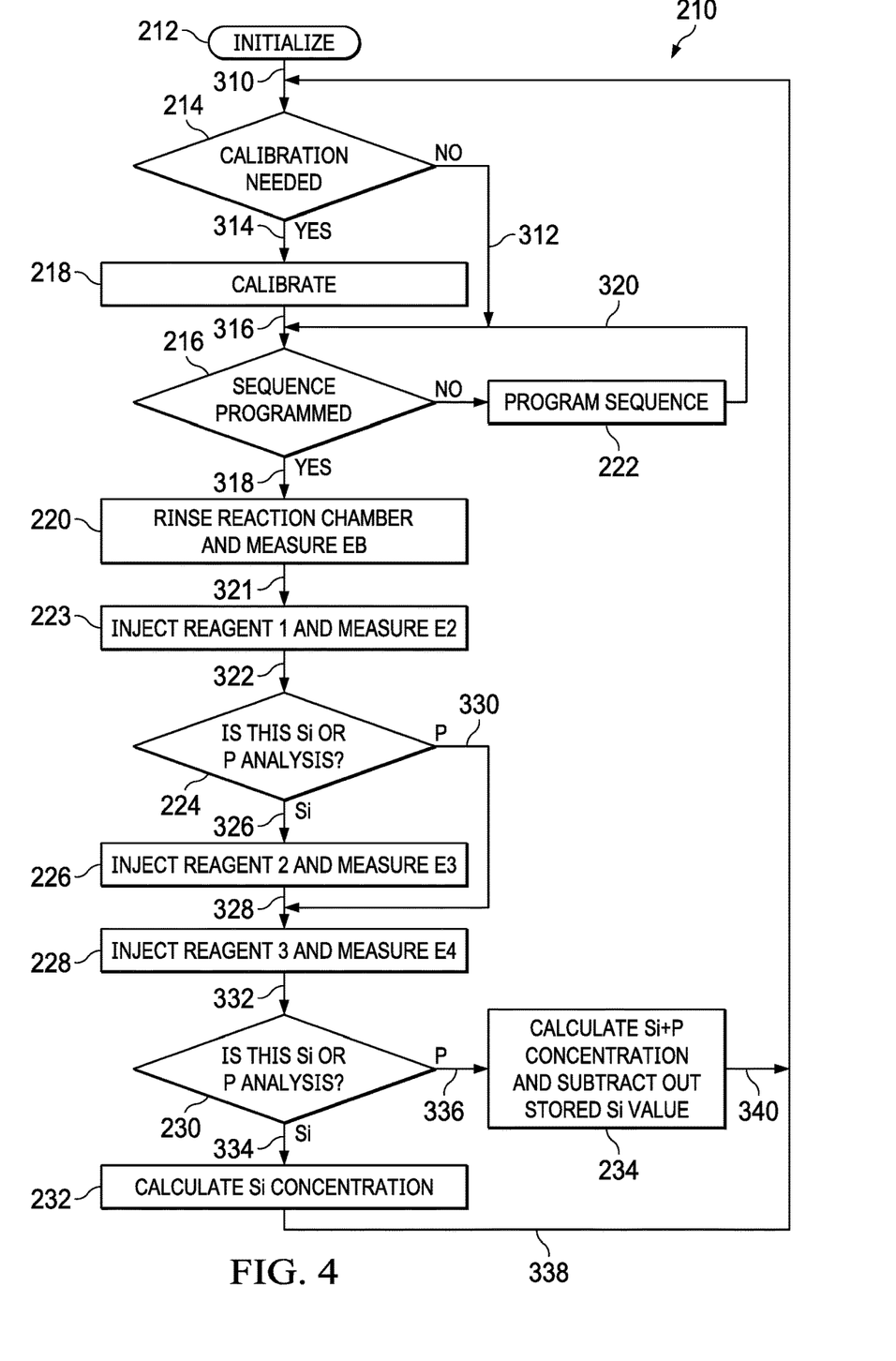
FIG. 4 is a flow diagram showing the algorithm programmed into a processor of the device incorporating the inventive concept.

Additional aspects of the inventive concept are illustrated in FIG. 4 as being achieved through proper programming of an algorithm 210 for a processor that operates the device 110 as described herein.

Algorithm 210 begins with an initialization step 212 of the device 110. In this step, status of the system is verified, including such items as verification of process flow, verification of system reagent availability and the like.

Once the system is initialized, the processor interrogates a memory unit thereof at step 214 to determine whether the device 110 needs to be calibrated. The need for calibration is indicated by a predetermined calibration threshold being exceeded. The calibration threshold at step 214 can be based on one or more of a variety of factors, such as, for illustrative purposes, the amount of time elapsed since the last calibration, the number of analyses performed since the last calibration, or the presence of an error message from a prior analysis performed. If no calibration is required, path 312 leads to step 216.

If a calibration is needed, path 314 leads to a calibration step 218, which must be performed before any further operation of the device. Calibration can be performed in a variety of manners, but a preferred manner includes the analysis of a known standard. After the calibration step 218 is performed, data from the calibration are stored in the memory unit and path 316 leads to step 216.

At step 216, the processor interrogates the memory unit thereof to determine if an analysis sequence has been stored by a user. Since the device 110 can perform an analysis for silica ("S") as well as an analysis for the combination of silica and phosphate ("C"), the analysis sequence can be represented as a series of "S" and "C" values. The first value in the sequence should always be an "S," and sequential "S" values may occur, but sequential "C" values would render the sequence invalid. By way of example, a sequence "SCSCSC" is a valid sequence but may test for phosphate more often than needed. A sequence "SSSCSSSCSSSC" is a valid sequence. Some sequences, such as "CSSCSS" (initial "C" value) or "SCCSSSC" (sequential "C" values), may be viable, but may be determined to be invalid under the algorithm as programmed. If a valid sequence is stored in memory, path 318 leads to step 220.

If no sequence or an invalid sequence is stored, path 320 leads to step 222. At that point, the user is required to enter a sequence, either by entering a sequence of "S" and/or "C" values or by selecting a predetermined sequence from a plurality of such predetermined sequences stored in memory. Upon entry of a sequence, path 320 leads back to step 216, where the entered sequence is verified as to validity, which then leads by path 318 to step 220.

With a valid sequence in place, step 220 becomes operative. The reaction chamber 40 is rinsed for a predetermined rinse time, typically a few minutes. At the end of the rinsing period, process fluid flow to the reaction chamber is stopped, retaining a sample in the reaction chamber. The 815 nm from the light source is detected at the photodetector, and, as the absorbance level at the photodetector stabilizes, a baseline absorbance $E_b$ is established and the value stored in memory. Path 321 leads the process to step 223.

At step 223, reactant pump 62 injects the aliquot of Reagent 1 from reagent bottle 52 into the sample and the reaction of the ammonium molybdate in an acidified aqueous medium is allowed to proceed. The reaction causes yellow molybdate complexes of the silica and phosphate present in the sample. While a nominal predetermined reaction time is programmed into the processor, the temperature of the sample may be taken into consideration in reducing the reaction time. The molybdate complexes of silica and phosphate will cause some absorbance of the 815 nm light during this step. The current at the photodetector is preferably monitored throughout the step and rate of change of the measured current at the photodetector may be used, in some circumstances, to determine that one or more of the reactions is effectively completed. The absorbance at the end of step 223 is stored in memory as E2 and path 322 leads to step 224.

Step 224 is an inquiry as to whether the analysis being performed in the sequence from step 216 is an "S" or a "C", in the algorithm 210 depicted in FIG. 4. It will be recognized that this inquiry could have been made prior to step 223, but the need for the information is not needed until this point, as the information can lead to a divergence of the process. If the analysis is an "S", path 326 leads to step 226. If the analysis is a "C", path 330 bypasses step 226 and leads directly to step 228.

In step 226, an aliquot of Reagent 2 (an aqueous solution of oxalic acid) is added to the reaction chamber 40 from reagent source 54 through pump 64, effected by signals from the processor. The oxalic acid reacts with any phosphate-molybdate complex present in the reaction chamber, breaking down the phosphate-molybdate complex into an optically inactive moiety, specifically one that does not absorb light at 815 nm. The oxalic acid does not appreciably affect the silica-molybdate complex present. After allowing the reaction to proceed for a predetermined reaction time, the current at the photodetector is again measured. The value of the current obtained, denominated E3, should be greater than E2, as no light absorbance should be attributable to the presence of phosphate. In an optional part of step 226, a comparison of E3 with Eb may be useful as an indicator of an error in the test, resulting in at least an error message. At the conclusion of step 226, path 328 leads to step 228.

At step 228, paths 328 and 330 come together. In the step, an aliquot of Reagent 3 is injected into the reaction chamber 40 from reagent source 56 through pump 66. Reagent 3 is an aqueous solution of potassium disulfite and 4-(methylamino)phenol hemisulfate salt which produces an intense blue color by reaction with the silica molybdate complex and (if the test sample has not gone through step 226) the phosphate molybdate complex. The blue color absorbs 815 nm light very strongly, so the amount of light received at the photodetector is reduced. This measured absorbance is designated as E4. At the conclusion of step 228, path 332 leads to step 230, which is again an inquiry into whether the analysis being performed is an "S" or a "C". If the analysis is an "S", path 334 leads to step 232. If the analysis is a "C", path 336 leads to step 234.

At step 232, the silica concentration is calculated using the Beer's Law relationship set out above. In preferred embodiments of the inventive concept, the calculated silica concentration from a predetermined number of the most recent "S" analyses is retained in memory, with the most recent concentration replacing the oldest concentration in stored values. These data can be used for a variety of purposes, including calculation of the phosphate content in a "C" analysis or the trending of silica concentration over time.

At step 234, the combined concentration of silica and phosphate is calculated using the Beer's Law relationship set out above. To obtain the phosphate concentration, the silica concentration needs to be subtracted out of the combined concentration. There are several options as to how this can be programmed into the algorithm. In one embodiment, the silica concentration from the immediately previous silica analysis is used. In another embodiment, the combined concentration is stored and the silica concentration used is the mean value of the silica analyses that occur before and after the combined analysis. In a yet further embodiment, a statistically calculated value is used, such as a mean value, of a silica concentration based upon a predetermined number of silica analyses occurring before and/or after the combined analysis to determine phosphate concentration.

In either case of an "S" or a "C" analysis, respective paths 338 or 340 lead back to step 214 and the system is ready for a further analysis.

In the preferred algorithms for operating the device, at least the most recent current values Eb (or E1), E2, E3 and E4 are stored in memory and even more preferably, several recent values of each are stored. Temperature values are also preferably stored, including at least the temperature in the heater 138, the temperature of the wall of the reaction chamber 40, and the ambient temperature. These latter two values may be used to estimate the temperature of the sample fluid, as temperature is known to affect the calculation involving Beer's law. The current values, and particularly Eb and E3, are known to be useful for detecting and troubleshooting diagnostic errors.

What is claimed is:

1. An apparatus for analyzing a water sample for both silica and phosphate content, comprising:
   an inlet for receiving a stream of the water sample to be tested;
   an exit for exhausting the water sample after testing;
   a flow conduit, providing a liquid flow path from the inlet to the exit;
   a reaction chamber, located in the flow conduit, sized to retain a predetermined volume of the water sample and comprising:
   a sample inlet in liquid communication with the inlet;
   a sample outlet in liquid communication with the exit;
   a plurality of reagent inlets; and
   a spectrometry apparatus comprising a window through which light is directed into the volume of the reaction chamber and a window through which the light is received by a photodetector;
   a valve for controlling flow through the flow conduit into the reaction chamber;
   a calibration feed system to provide a calibration fluid to the flow conduit upstream of the valve;
   a plurality of reagent feed systems, each of which is in fluid communication with one of the plurality of reagent inlets; and
   a processor, in communication with a database, the spectrometry apparatus, the valve and the plurality of reagent feed systems, programmed to operate the apparatus to perform, as requested, any one of the following procedures:
   a calibration procedure;
   a silica content analysis; and
   a phosphate content analysis, comprising the steps of:
   providing, in the reaction chamber, a water sample to be analyzed;
   adding an aliquot of an aqueous solution of ammonium molybdate and an inorganic acid, to react with silica and phosphate in the water sample, producing colored silica and phosphate complexes,
   passing light from a light source across the reaction chamber through the water sample containing the colored silica and phosphate complexes to the photodetector, measuring the current generated thereby in the photodetector and storing the current as a first combined value in the database;
   adding an aliquot of an aqueous solution of potassium disulfite and 4-(methylamino)phenol hemisulfate salt to the water sample containing the colored silica and phosphate complexes, to react with the colored silica complexes and the colored phosphate complexes, both of which are converted into more intensely colored complexes;
   passing light from the light source across the reaction chamber through the water sample, containing the more intensely colored complexes, to the photodetector, measuring the current generated thereby in the photodetector and storing the current as a second combined value in the database;
   calculating, in the processor, a value of a combined silica and phosphate content in the water sample from a relationship between the second combined value and the first combined value; and
   calculating and reporting, in the processor, a phosphate content by subtracting a value of a most-recently stored silica content from the combined silica and phosphate content.

2. The apparatus of claim 1, further comprising:
   a heater, positioned in the flow conduit between the inlet and the valve, for selectively heating the water sample passing therethrough.

3. The apparatus of claim 1, wherein;
   each reagent feed system comprises a reagent container and a metering pump, selectively actuated by the processor to provide a predetermined amount of a selected reagent to one of the reagent inlets.

4. The apparatus of claim 1, wherein the calibration feed system further comprises a calibration fluid container and a metering pump, selectively actuated by the processor.

5. The apparatus of claim 2, wherein the calibration feed system further comprises a further valve, positioned in the flow conduit between the inlet and the heater, to provide the calibration fluid to the flow conduit upstream of the heater.

6. The apparatus of claim 1, wherein the light source is a monochromatic light source that produces near-infrared light at 815 nm.

7. The apparatus of claim 1, wherein the silica content analysis performed by the apparatus at the instruction of the processor comprises the steps of:
   providing, in the reaction chamber, a water sample to be analyzed;
   adding an aliquot of an aqueous solution of ammonium molybdate and an inorganic acid, to react with silica and phosphate in the water sample, producing colored silica and phosphate complexes,
   passing light from the light source across the reaction chamber through the water sample containing the colored silica and phosphate complexes to the photodetector, measuring the current generated thereby in the photodetector and storing the current as a first silica value in the database;
   adding an aliquot of an aqueous solution of oxalic acid to the water sample containing the colored silica and phosphate complexes, to react only with the colored phosphate complexes, which are converted into an optically-inactive phosphate moiety;
   passing light from the light source across the reaction chamber through the water sample containing the colored silica complexes and the optically-inactive phosphate moiety to the photodetector, measuring the current generated thereby in the photodetector and storing the current as a second silica value in the database;
   adding an aliquot of an aqueous solution of potassium disulfite and 4-(methylamino)phenol hemisulfate salt to the water sample containing the colored silica complexes and optically-inactive phosphate moiety, to react with the colored silica complexes and the optically-inactive phosphate moiety, intensifying the color of the colored silica complexes;
   passing light from the light source across the reaction chamber through the water sample, containing the more intensely colored silica complexes, to the photodetector, measuring the current generated thereby in the photodetector and storing the current as a third silica value in the database;
   calculating and reporting, in the processor, the value of the silica content in the water sample from a relationship between the third silica value and at least one of the first and second silica values; and
   storing in the database, the calculated silica value.

8. The apparatus of claim 1, wherein the calibration procedure performed by the apparatus at the instruction of the processor comprises the steps of:
- providing, in the reaction chamber, a sample of the calibration fluid from the calibration feed system; and
- performing as determined by the processor, in the reaction chamber, either the silica content analysis or the phosphate content analysis.

9. The apparatus of claim 7, wherein the step of providing the water sample to be analyzed is achieved by sub-steps comprising:
- rinsing the reaction chamber with the water to be sampled by flowing the water to be sampled therethrough;
- stopping the flow through the reaction chamber of the water to be sampled, retaining a water sample in the reaction chamber; and
- passing light from the light source across the reaction chamber through the water sample to the photodetector, measuring the current generated thereby in the photodetector and storing the current as a baseline value in the database.

10. The apparatus of claim 1, wherein the step of providing the water sample to be analyzed is achieved by sub-steps comprising:
- rinsing the reaction chamber with the water to be sampled by flowing the water to be sampled therethrough;
- stopping the flow through the reaction chamber of the water to be sampled, retaining a water sample in the reaction chamber; and
- passing light from the light source across the reaction chamber through the water sample to the photodetector, measuring the current generated thereby in the photodetector and storing the current as a baseline value in the database.

* * * * *